United States Patent
Haikarainen et al.

(10) Patent No.: US 6,810,873 B1
(45) Date of Patent: Nov. 2, 2004

(54) POWDER INHALER FOR COMBINED MEDICAMENT

(75) Inventors: Jussi Haikarainen, Helsinki (FI); Kari Seppälä, Helsinki (FI); Tommi Koskela, Kuopio (FI); Antti Koivisto, Kuopio (FI); Matti Silvasti, Kuopio (FI)

(73) Assignee: Innovata Biomed Limited, Edinburgh (GB)

( * ) Notice: Subject to any disclaimer, the term of this patent is extended or adjusted under 35 U.S.C. 154(b) by 0 days.

(21) Appl. No.: 09/959,213

(22) PCT Filed: Apr. 20, 2000

(86) PCT No.: PCT/FI00/00347

§ 371 (c)(1),
(2), (4) Date: Jan. 16, 2002

(87) PCT Pub. No.: WO00/64519

PCT Pub. Date: Nov. 2, 2000

(30) Foreign Application Priority Data

Apr. 23, 1999 (FI) .................................................. 990913

(51) Int. Cl.[7] .......................... A61M 16/00; A61M 15/00
(52) U.S. Cl. ................................. 128/203.15; 128/203.19
(58) Field of Search ....................... 128/200.11–200.13, 128/200.17–200.19, 200.21–200.23, 203.12, 203.13, 203.15, 203.19, 203.21, 203.22, 200.24; 604/58, 62, 64

(56) References Cited

U.S. PATENT DOCUMENTS

| | | | | |
|---|---|---|---|---|
| 3,874,381 A | * | 4/1975 | Baum ..................... | 128/200.14 |
| 5,002,048 A | * | 3/1991 | Makiej, Jr. ............. | 128/200.23 |
| 5,007,419 A | * | 4/1991 | Weinstein et al. ....... | 128/20.23 |
| 5,169,029 A | * | 12/1992 | Behar et al. ................... | 222/1 |
| 5,208,226 A | * | 5/1993 | Palmer ....................... | 514/171 |
| 5,524,613 A | | 6/1996 | Haber et al. | |
| 5,575,280 A | * | 11/1996 | Gupte et al. ........... | 128/203.15 |
| 5,664,557 A | * | 9/1997 | Makiej, Jr. ............. | 128/200.23 |
| 5,857,457 A | * | 1/1999 | Hyppola ................ | 128/203.15 |
| 5,904,139 A | * | 5/1999 | Hauser .................. | 128/200.23 |
| 5,941,241 A | * | 8/1999 | Weinstein et al. ..... | 128/200.23 |
| 6,543,443 B1 | * | 4/2003 | Klimowicz et al. .... | 128/200.23 |
| 6,553,987 B1 | * | 4/2003 | Davies ................. | 128/200.14 |
| 2003/0116157 A1 | * | 6/2003 | Braithwaite et al. ... | 128/203.15 |
| 2003/0136406 A1 | * | 7/2003 | Seppala ................. | 128/203.15 |

* cited by examiner

Primary Examiner—Henry Bennett
Assistant Examiner—Teena Mitchell
(74) Attorney, Agent, or Firm—Finnegan, Henderson, Farabow, Garrett & Dunner, LLP (57) ABSTRACT

The invention relates to a multidose powder inhaler for the dispensing of a powdered medicament by inhalation. The device comprises two or more medicament containers for different drug powders which are inhaled as a combined medication, and separate aerosolization channels for each drug powder. The device of the invention is useful, for example, in the treatment of asthma.

6 Claims, 6 Drawing Sheets

POWDER INHALER FOR COMBINED MEDICAMENT

This application is a national stage filing of PCT International Application No. PCT/FI00/00347, filed on Apr. 20, 2000, which published in the English language. This application also claims the benefit of priority under 35 U.S.C. § 119(a) to Finnish patent application no. 990913, filed on Apr. 23, 1999.

BACKGROUND OF THE INVENTION

The present invention relates to a device for dispensing of a powdered drug preparation by inhalation. The device is in particular a multiple-dose device without propellant gas, equipped with a metering means which dispenses doses from a powder container. The device comprises two or more powder containers for different drug powders which can be inhaled as a combined medication. The device of the invention is useful, for example, in the treatment of asthma.

The administering of a powdered drug preparation by inhalation from an inhaler is known. Multiple-dose type powder inhalers comprising a flow container which holds the drug and a metering member which measures and dispenses a unit dose are also known, for example from patent publications GB 2165159, EP 79478, and EP 166294. In these devices, a series of dosing recesses are notched into the surface of a cylindrical metering member, and the said member is disposed in a chamber of precisely the same shape. When the metering member is rotated, the dosing recesses in turn will move first to a position in alignment with the powder container for being filled and thereafter to a position in alignment with the inhalation channel, whereupon a unit dose will fall by gravity from the dosing recess into the inhalation channel. Thereafter the dose of medicament is inhaled from the inhalation channel. These devices have the drawback that they make overdosing of the medicament possible by allowing the dispensing of a plurality of doses in succession into the inhalation channel, whereby a multiple dose may be drawn by one inhalation.

Attempts have been made to solve the above-mentioned problem by using dispensing systems in which the dosing recess will not be emptied into the inhalation channel by gravity but, instead, the dose of medicament is inhaled directly from the dosing recess, as disclosed in patent publications WO 92/00771 and WO 92109322. When the metering member is rotated, the dosing recesses will move first to a position in alignment with the flow container for filling, and then to the inhalation channel, which is shaped so that the dosing recess will be emptied under the effect of the air flow being inhaled, and thereafter, having rotated through a full 360°, back to a position in alignment with the flow container.

In the treatment of respiratory disorders it is often beneficial to administer a combination of drugs, e.g. combination of a bronchodilator and an anti-inflammatory drug to a patient. The devices described above are not capable to deliver more than one drug powder at a time. Even though it is in some cases possible to mix two or several drugs into an inhalable powder mixture to be administered simultaneously as a single dose, the incompatibility of the drug substances, interactions during storage or different aerosolization properties may often prevent the use of such drug mixture. Therefore, in order to inhale a combined medication the patient may have to inhale different drug powders from two powder inhalers. A multi-container powder inhaler has been earlier described in U.S. Pat. No. 5,524,613. However, this device is complex and requires a pressurized air source to aid the inhalation process. Furthermore, each powder is aerosolized in a common air channel, which does not take into account different aerosolization properties of the powders.

Therefore, there is a need for a simple low-cost multi-dose powder inhaler, which is able to deliver a combined medication by a single inhalation; and which takes into account different aerosolization properties of different medicament powders.

SUMMARY OF THE INVENTION

The present invention is related to a multi-dose powder inhaler capable of delivering a combined medicament, e.g. bronchodilator and an anti-inflammatory drug, simultaneously by a single inhalation. Rather than having a powder container for a mixture of the active ingredients, the inhaler comprises two powder containers from which doses needed for the combined administration are metered, brought to the air channel and inhaled simultaneously. Preferably the two containers contain different active ingredients. The active ingredients are in the separate containers, are brought to the air channel by separate dosing recesses and are mixed not earlier than in the air channel or in the respiratory tract of the patient during inhalation. Importantly, the inhaled air stream is conducted via two separate aerosolization channels, one for each medicament powder. Accordingly, the differences in the aerosolization properties of each medicament powder can be taken into account and each aerosolization channel can be designed according to the properties of each medicament powder.

The inhaler of the present invention is able deliver and deaggregate medicament powder from two or more dosing recesses simultaneously without the use of pressurized air even if used by a patient having reduced inhalation capacity.

BRIEF DESCRIPTION OF THE DRAWINGS

FIG. 5b is a cross sectional view taken along line A—A of FIG. 5a.

FIG. 6b is a cross sectional view taken along line A—A of FIG. 6a.

DETAILED DESCRIPTION OF THE INVENTION

The present invention provides a device for dispensing powdered medicament by inhalation, comprising a first and a second medicament container for receiving a plurality of medicament doses; a metering member equipped with a first and a second dosing recesses for receiving in one position a metered dose of the powdered medicament from the first and the second medicament container and for bringing in another position the metered dose of the powdered medicament from the first and the second medicament container to the first and second aerosolization channels where the metered doses are discharged simultaneously to the inhaled air upon inhalation.

The present invention also provides a method for inhaling a dose of first and second powdered medicaments comprising: a) providing an inhaler with an air flow path and supply of the first and second powdered medicaments, b) metering a dose of the first and second powdered medicaments simultaneously from the supply of the first and second powdered medicaments, c) bringing the metered dose of the first and second powdered medicaments simultaneously into the air flow path of the inhaler, wherein the first and the second powdered medicaments each has own separate air flow paths at the region of aerosolization of the powdered medicament, and d) inhaling the metered dose of the first and second powdered medicaments through the inhaler.

The first and the second medicament containers are separated so that the active ingredients can not be mixed during storage. The containers contain, in the powder form, preferably different active ingredients which are to be delivered to a patient as a combined medication. Such combined medication can be a combination of any two drugs which can be administered by inhalation. In the treatment of asthma a typical combination is a combination of a bronchodilator and an anti-inflammatory drug. The anti-inflammatory drug is preferably a steroidal anti-inflammatory drug. Suitable combinations include e.g. formoterol and budesonide, salmeterol and beclomethasone dipropionate, and salmeterol and fluticasone propionate. Normally, the container have a supply of medicament for e.g. 200 doses.

The metering member, which can be in any suitable form, is manually actuatable and equipped with at least one dosing recess for metering a dose from the first medicament container and at least one dosing recess for metering a dose from the second medicament container. Several metering member forms for multi-dose powder inhalers are known in the art, e.g. a rotatable dosing drum as described in e.g. WO 92/00771 and WO 92/09322, a movable dosing slide as described in e.g. WO 95/31237 and WO 97/17097 or a dosing rod as described in e.g. WO 92118188 and U.S. Pat. No. 5,263,475. Preferably the metering member is in the form of a drum, slide or rod. However, also other forms of metering members can be used in the device of the invention. The only requirement for the metering member is that it can be equipped with a first and a second dosing recess for receiving in one position a metered dose of the powdered medicament from the first and the second medicament container and for bringing in another position the metered dose of the powdered medicament from the first and the second medicament container to the first and second aerosolization channels.

An important feature of the device of the invention is that the inhaled air stream is conducted via two separate aerosolization channels one for each medicament powder. This provides a significant advantage as the cross-sectional shape and dimensions of each aerosolization channel can then be designed according to the aerosolization and deaggregation properties of each medicament powder, e.g. to produce different air flow resistance for each medicament powder. When two separate aerosolization channels are used, the two active ingredients are mixed with each other not earlier than in the mouthpiece or, if the separate aerosolization channels are led throughout the mouthpiece, in the mouth of the patient. Preferably the metered doses are discharged and aerosolized to the inhaled air upon inhalation directly from the dosing recesses, whereby the possibility of overdosing by inhaling multiple doses is avoided.

The aerosolization channels are preferably designed so that at the beginning of the inhalation air is led directly into the filled dosing recesses which are then intensively flushed by the inflowing air, and the powder is aerosolized simultaneously from the first and the second dosing recesses.

In case the metering member is in the form of a rotatable drum, e.g. a cylinder, it is equipped with two series of dosing recesses notched into the peripheral surface of the metering drum. In the first position of the metering drum the fist dosing recess is in alignment with the first medicament container and, simultaneously, the second dosing recess is in alignment with the second medicament container, for being filled with the powder. When the metering member is rotated to the second position, the filled first and the second dosing recesses are moved to the first and second aerosolization channels for inhalation.

In case the metering member is in the form of a rod, the metering member may consist of a pair of rods movable along their longitudinal axis. The first rod is equipped with a first dosing recess and is movable through the first medicament container. The second rod is equipped with a second dosing recess and is movable through the second medicament container. The dosing recess can be in the form of cavity or hole located at the other end of the metering rod. In one position of the rod the recess is inside the medicament container and filled with the powder. In other position of the rod the recess filled with powder is brought out of the medicament container into the aerosolization channel. The rods may be attached to the common actuating member in order to achieve simultaneous movement of the rods between the two positions.

The device of the invention is further illustrated below by way of examples, with reference to FIGS. 1 to 6b.

Figure 1:
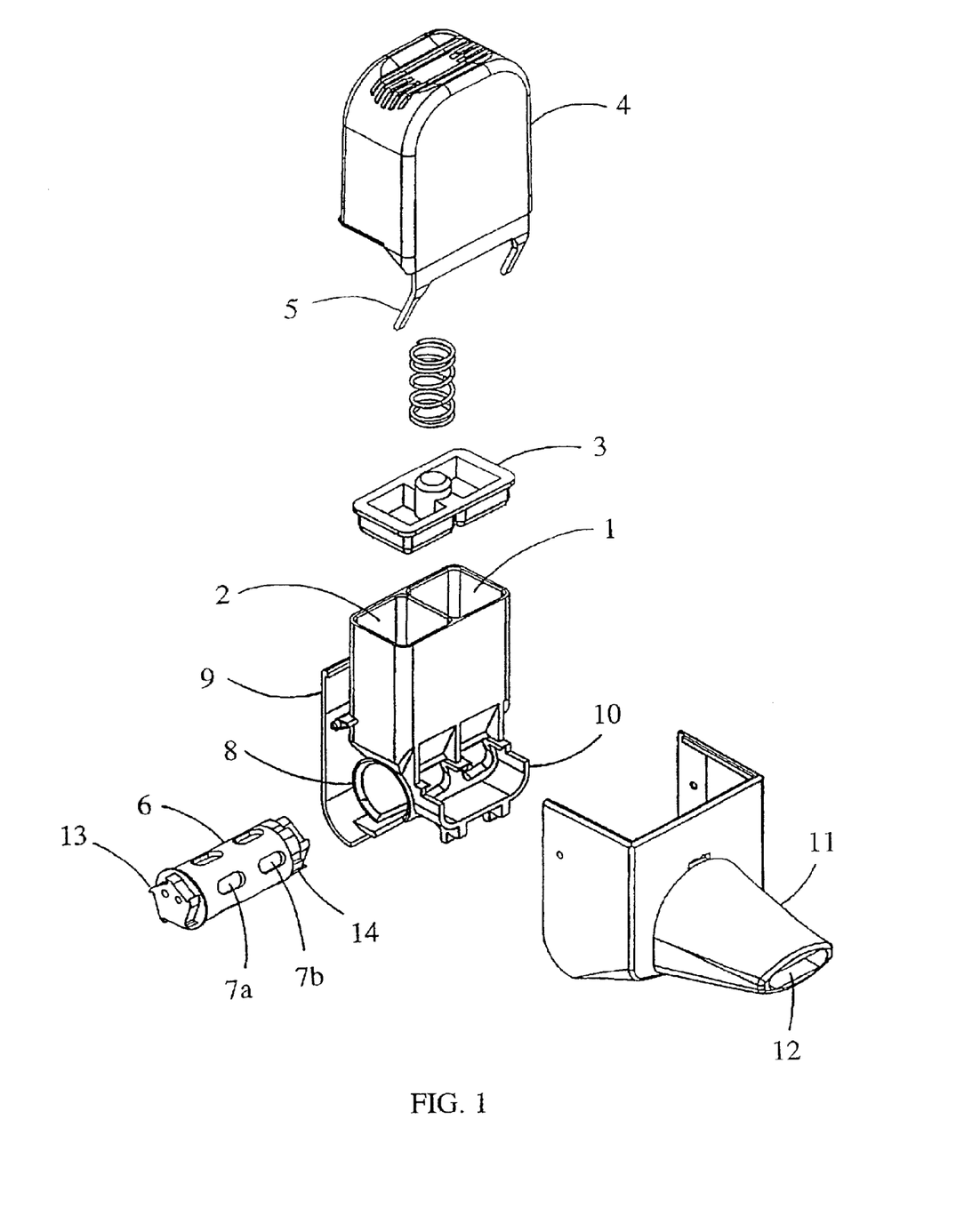
FIG. 1 is an explosive perspective view of a first embodiment of the device of the invention.

In FIG. 1 the structure of a first embodiment of the device of the invention comprising a rotatable metering drum is shown in an explosive view. The first and second medicament containers (1,2) which are to be filled with the powdered medicament have a square cross-section and conical end portions. A lid (3) closes the upper edge of the medicament containers. The cover (4) together with a flap (5), the function of which will be explained below, is adapted to cover the medicament containers (1,2) and the lid (3). A manually rotatable metering drum (6) having two series of five dosing recesses (7a, 7b) is mounted to the hollow cylindrical body (8) which is moulded together with the medicament containers (1,2).

Moulded together with the medicament containers is also the rear wall (9) of the device as well as the projection (10) to receive the mouthpiece (11) with the aerosolization channels. The metering member (6) has, in addition to the series of dosing recesses, teeth (13) which are engaged with the flap (5). The device is actuated by pressing down the cover, whereby the flap (5) engaged with the teeth (13) causes the metering member rotate so that rotation can only be accomplished stepwise corresponding to the peripheral distance between the dosing recesses. The detent drive of the metering member automatically aligns the dosing recesses with the outlet of the medicament container on the one side and the aerosolization channel of the mouthpiece on the other side. Furthermore, the cylindrical body has an extended detent nose (not shown) which engages into notches (14) in the metering drum such that analogue to a ratchet rotation is only possible to one direction.

Figure 2:
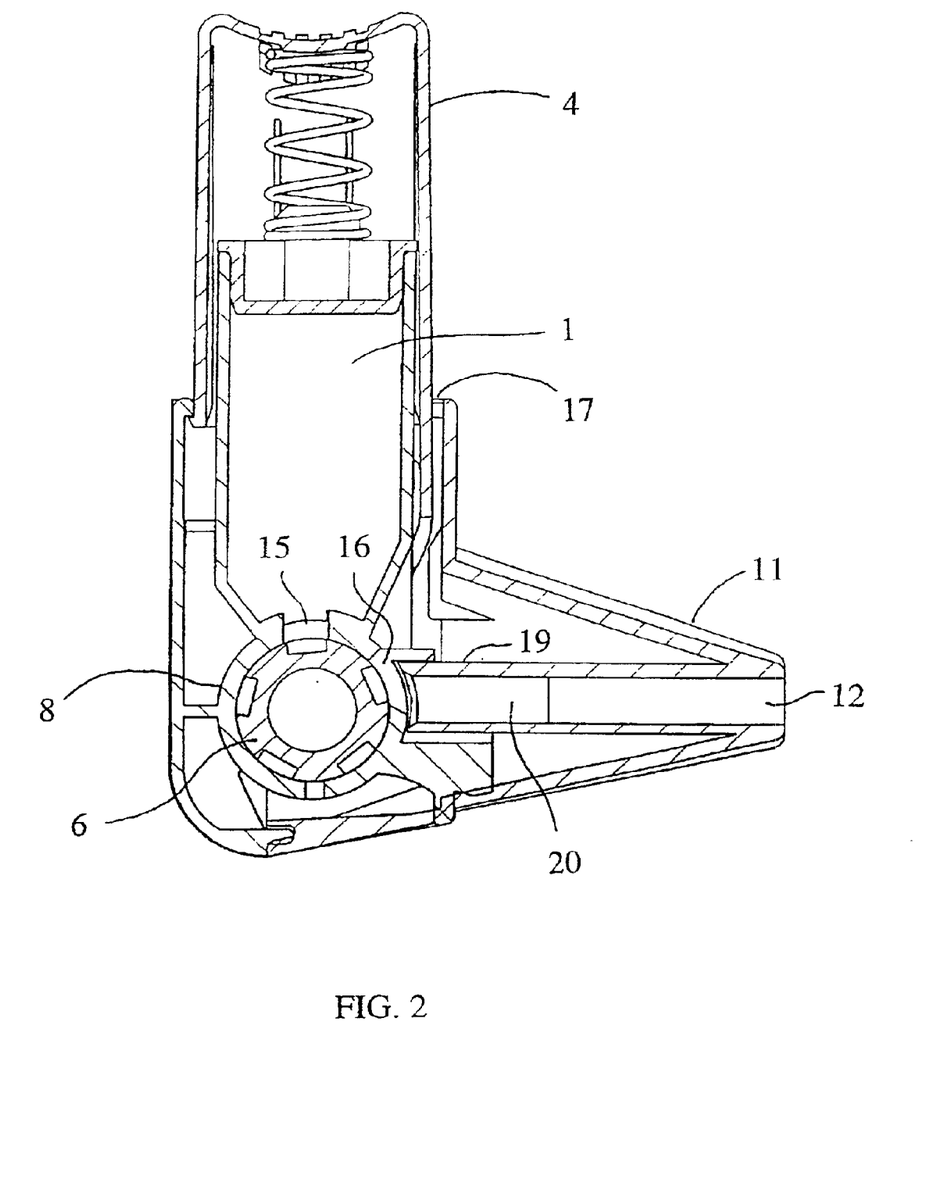
FIG. 2 is a longitudinal cross-section of the device of FIG. 1 through a first medicament container.

In FIG. 2 a longitudinal section through the first medicament container of the first embodiment of the device is shown. The cylindrical body (8) has an opening (15) through which powder can fall from the medicament container to the dosing recess when the dosing recess is in alignment with the opening (15). Another opening (16) is provided at the level of the aerosolization channel (20) for discharging the powder from the dosing recess to the aerosolization channel upon inhalation. In the position shown in FIG. 2 the upper dosing recess is just being filled with the dose of the first medical powder from the first medicament container, while the earlier filled dosing recess has turned to the aerosolization channel and is ready to be inhaled. The mouthpiece (11), through which the medical powder can be inhaled, is formed at one side of the inhalation device and has an aerosolization channel (20) for distribution of the dose of medicament from the dosing recess into the flow of breathing air. In the area where the mouthpiece is attached, air intakes (17) are provided. The intaken air is led to a slot between the opening (16) of the cylindrical body and a partition wall (19) of the mouthpiece. The slot, which is preferably moulded as a nozzle, provides strongly aligned stream of air to the dosing recess blowing the powder out from the dosing recess into the aerosolization channel without leaving any residue.

Figure 3A:
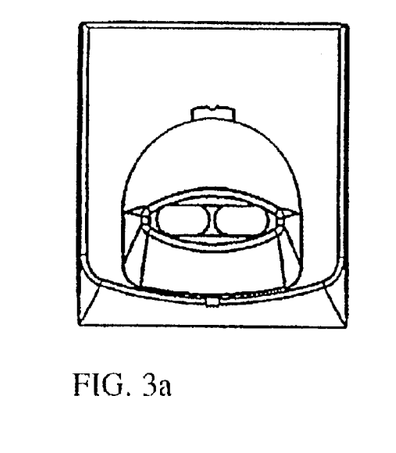
FIGS. 3a, 3b, 3c and 3d are a front view, a cross section viewed from the side, back view and a cross section viewed from above, of one embodiment of the mouth piece.
Figure 3B:
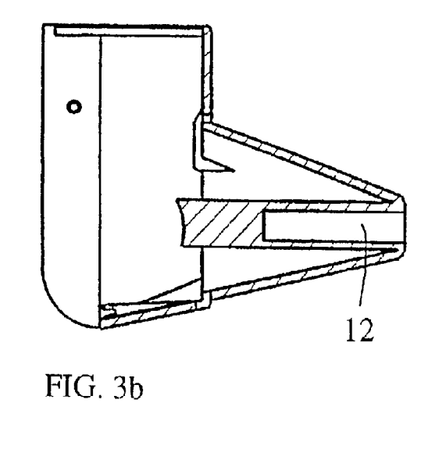
Figure 3C:
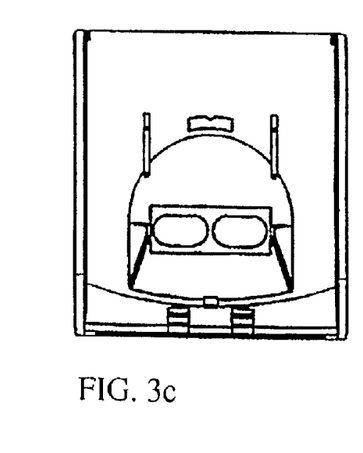
Figure 3D:
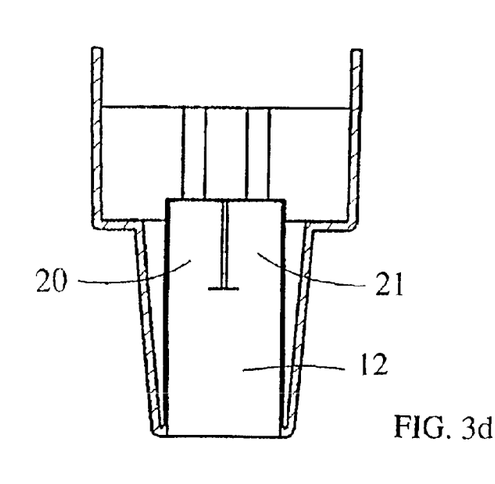

FIGS. 3a, b, c and d show one embodiment of the mouthpiece comprising two separate aerosolization channels (20, 21) which are united in the mouthpiece to the main air channel (12). In this embodiment the active ingredients are mixed with each other not earlier than in the main air channel in the mouthpiece.

Figure 4A:
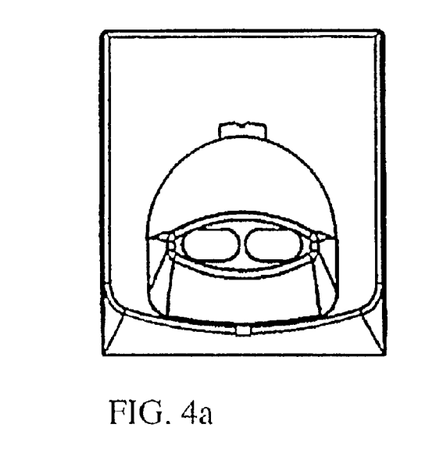
FIGS. 4a, 4b, 4c and 4d are a front view, a cross section viewed from the side, back view and a cross section viewed from above, of a second embodiment of the mouth piece.
Figure 4B:
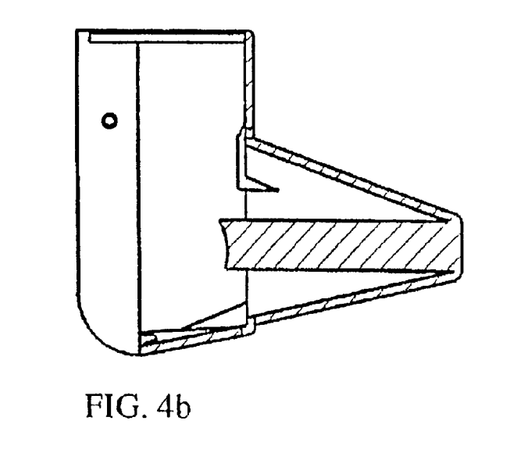
Figure 4C:
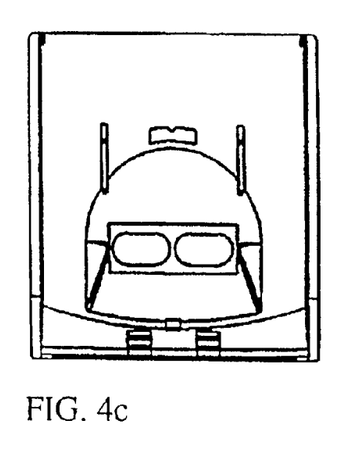
Figure 4D:
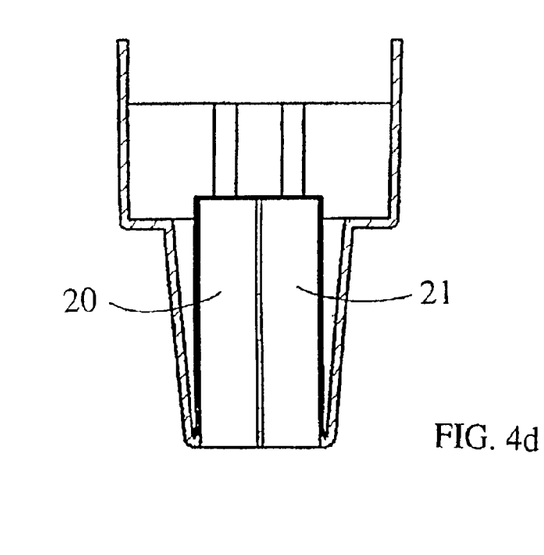

FIGS. 4a, b, c and d show another embodiment of the mouthpiece comprises two separate aerosolization channels (20, 21) which are led throughout of the mouthpiece. In this embodiment the active ingredients are mixed with each other not earlier than in the mouth or respiratory tract of the patient.

FIGS. 5a to 6b show another embodiment of the device comprising an axially movable pair of metering rods. The medicament containers (1,2) which are to be filled with the powdered medicament have a square cross-section and conical end portions. The containers are secured to the outer casing (27) by snapfastening means A lid (22) closes the upper edge of the medicament containers. The axially movable cover (23) is adapted to cover the medicament containers (1,2) and the lid (22). The cover (23) is attached to the outer casing (27) by snapfastening means. The cover (23) is urged upward by a spring (not shown) secured between the lid (22) and the cover (23). A pair of metering rods (6) having a hole-formed dosing recesses (7a, 7b) in the flattened lower portion is attached to the axially movable cover. The pair of metering rods (6) is slidably mounted through the lid (22) so that the first metering rod extends throughout the interior of the first medicament container and the second metering rod extends throughout the interior of the second medicament container. The bottom of the conical part of each container has an opening adapted to receive the flattened lower portion of the metering rod. The metering rods have projections (26) for agitation of the powder in the container as the rod slides between its first and second position.

Fixed to the medicament containers are the aerosolization channels (20, 21) as well as the chamber for the remnants (24) for removing any powder possibly left in the aerosolization channel after the movement of the metering rods. In this embodiment the aerosolization channels (20, 21) unite in the mouthpiece (11) to the main air channel (12). Thus, in this embodiment the active ingredients are mixed not earlier than in the main air channel of the mouthpiece. The two separate aerosolization channels (20, 21) may also be kept separate throughout the mouthpiece, in which case the active ingredients are mixed not earlier than in the mouth or the respiratory tract of the patient.

Figure 5A:
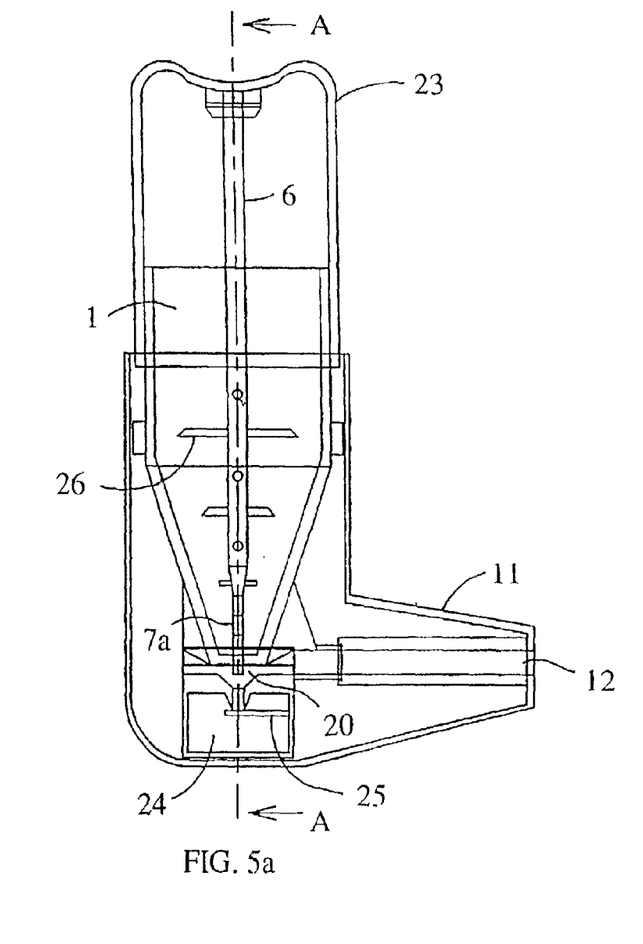
FIG. 5a is a side view of a second embodiment of the device of the invention in the filling position.
Figure 5B:
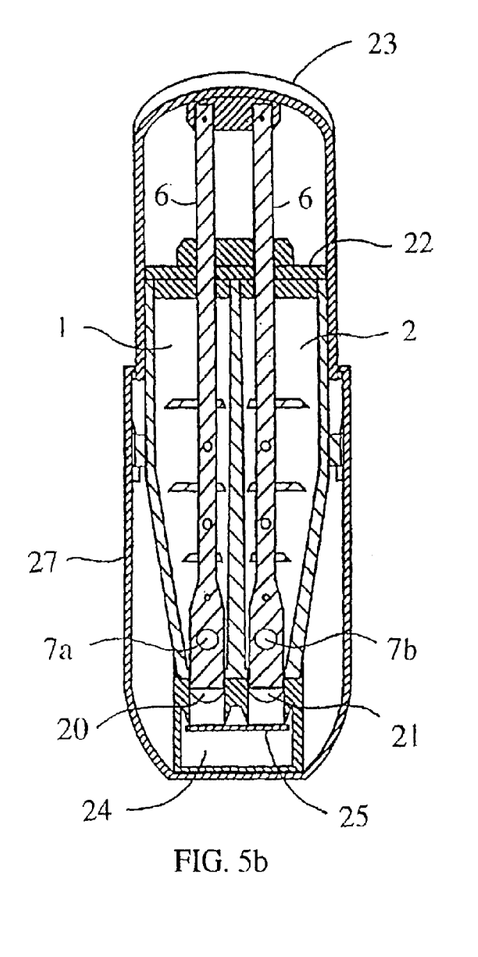

FIGS. 5a and b show the metering rods (6) in the inhalation position. The hole-formed dosing recesses (7a, 7b) are in the medicament container and are filled with the powder. The flattened lower portion of each rod extends slightly through the slot of the container bottom thereby preventing the flow of powder from the container through the slot.

Figure 6A:
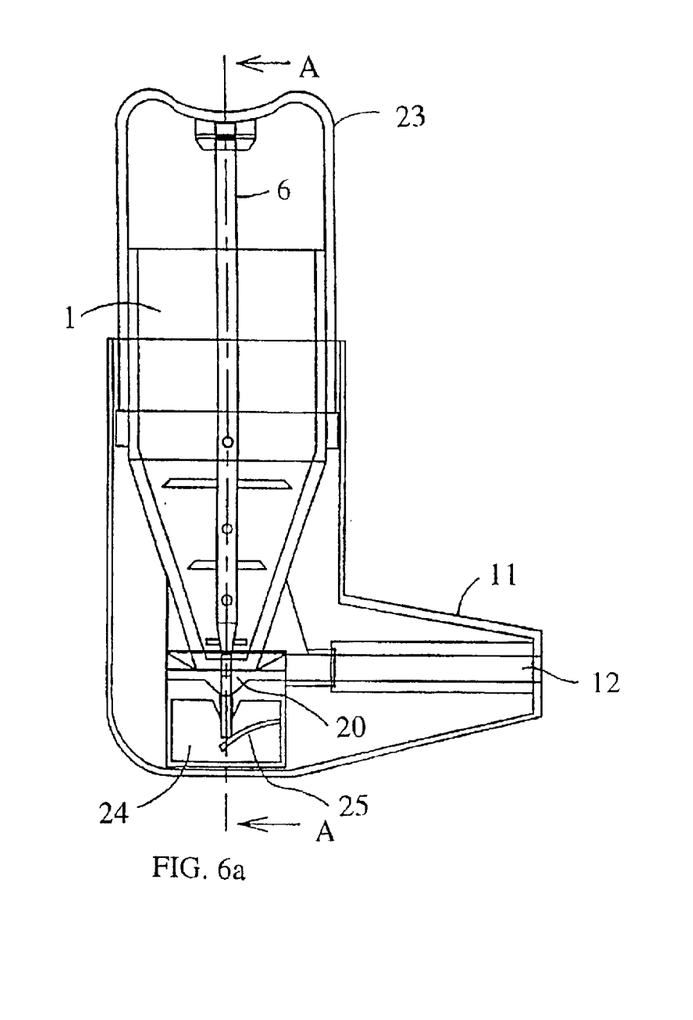
FIG. 6a is a side view of the second embodiment of the device of the invention in the inhalation position.
Figure 6B:
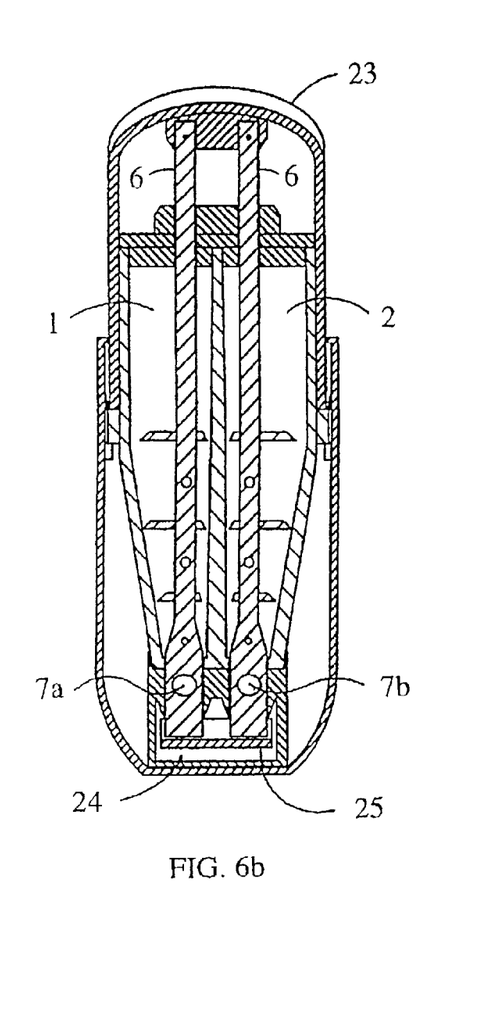

In FIGS. 6a and b the cover (23) has been depressed and the dosing recesses (7a, 7b) have been moved simultaneously to the corresponding aerosolization channels (20, 21). Each dosing recess has stopped at the level of the slanted floor of the aerosolization channel and the dose is ready to be inhaled via mouthpiece. The powder is inhaled directly from the dosing recesses (7a, 7b) while the cover is depressed. After inhalation the cover is released and the metering rods (6) return to the filling positions. After the metering rods have returned back to the filling position any powder left in the aerosolization channels (20, 21) tend to fall to the chamber of remnants (24). The chamber of remnants is closed by the closure member (25) which is engaged with the tip of the metering rod (6) so that the closure member is opened when the metering rod is in the inhalation position.

Other modifications and variations can be made to the disclosed embodiments without departing from the subject of the invention as defined in the following claims. For example, more than two medicament containers and corresponding series of dosing recesses could be used. In addition, a counter could be mounted to the inhaler to count the number of rotations of the dosing member. It is considered to be routine for one skilled in the art to make such modifications to the device of the invention.

What is claimed is:

1. A device for dispensing powdered medicament by inhalation, comprising
    a first and a second medicament container for receiving a plurality of medicament doses;
    a metering member equipped with a first and a second dosing recess adapted to receive in one position of the metering member a metered dose of a powdered medicament from the first and from the second medicament containers; and
    a first and a second aerosolization channel, wherein the first and the second dosing recesses are adapted to bring in another position of the metering member the metered doses of the powdered medicament to the first and the second aerosolization channels, where the metered doses are discharged simultaneously to inhaled air upon inhalation via a mouthpiece.

2. A device of claim 1, wherein the first and the second aerosolization channels are led separately throughout the mouthpiece.

3. A device of claim 1, wherein the first and the second aerosolization channels are united in the mouthpiece to form a main air channel.

4. A device of claim 1, wherein the metered doses are discharged to inhaled air directly from the first and the second dosing recesses upon inhalation.

5. A method for inhaling a dose of first and second powdered medicaments comprising
    a) providing an inhaler with an air flow path and supply of the first and second powdered medicaments,
    b) metering a dose of the first and second powdered medicaments simultaneously from the supply of the first and second powdered medicaments,
    c) bringing the metered dose of the first and second powdered medicaments simultaneously into the air flow path of the inhaler, wherein the first and the second powdered medicaments each has their own separate air flow paths at the region of aerosolization of the powdered medicament, and
    d) inhaling the metered dose of the first and the second powdered medicaments through the inhaler.

6. A method of claim 5, wherein the first powdered medicament comprises a bronchodilator and the second powdered medicament comprises an anti-inflammatory drug.

* * * * *